US012766268B2

(12) United States Patent
Konana Thippeswamy et al.

(10) Patent No.: US 12,766,268 B2
(45) Date of Patent: Oct. 20, 2026

(54) DUAL CHAMBER SYRINGE WITH MANUALLY ACTUATED, CHAMBER ISOLATION VALVE

(71) Applicant: Becton, Dickinson and Company, Franklin Lakes, NJ (US)

(72) Inventors: Vivek Konana Thippeswamy, Bengaluru (IN); Anandhakannan Rajugovindasamy, Coimbatore (IN); Sandip Satishsonar, Dist-Sangli (IN); Tharanath E., Bengaluru (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 625 days.

(21) Appl. No.: 18/071,888

(22) Filed: Nov. 30, 2022

(65) Prior Publication Data

US 2024/0173479 A1 May 30, 2024

(51) Int. Cl.
*A61M 5/315* (2006.01)
*A61M 5/178* (2006.01)
(Continued)

(52) U.S. Cl.
CPC ........ *A61M 5/31596* (2013.01); *A61M 5/178* (2013.01); *A61M 5/19* (2013.01); *A61M 5/3134* (2013.01)

(58) Field of Classification Search
CPC .... A61M 5/1407; A61M 5/1409; A61M 5/19; A61M 5/2448; A61M 5/284; A61M 5/31596; A61M 2005/2451; A61M 2005/2787; A61M 2005/31598; A61M 2039/2473; A61M 2039/2486
See application file for complete search history.

(56) References Cited

U.S. PATENT DOCUMENTS 984,037 A 2/1911 Sheets
3,680,558 A 8/1972 Kapelowitz
(Continued)

OTHER PUBLICATIONS

PCT International Search Report and Written Opinion in PCT/US2023/081542 dated Apr. 4, 2024, 14 pages.
(Continued)

*Primary Examiner* — Kami A Bosworth
(74) *Attorney, Agent, or Firm* — Servilla Whitney LLC

(57) ABSTRACT

A dual chamber syringe facilitates selective drug mixing, dosing, and administration through catheters or other vascular accessing devices (VADs), as well as pre- or post-administration flushing of catheters with a single syringe instrument. A syringe barrel incorporates an outlet, such as a Luer connector, variable-volume, primary and secondary fluid chambers, with nested respective plungers, with plunger rods capable of selective translation within the barrel interior along a common axis, and plunger stoppers. An externally accessible, selectively resealable, manual valve disposed within the barrel interior, selectively isolates the secondary fluid chamber from fluid communication with the primary fluid chamber and/or the outlet of the syringe barrel. Selective manipulation of the valve facilitates aspiration into or discharge from either of the chambers separately or jointly. In some embodiments, the syringe is prepackaged with flushing solution in the secondary fluid chamber.

18 Claims, 10 Drawing Sheets

(51) Int. Cl.
*A61M 5/19* (2006.01)
*A61M 5/31* (2006.01)

(56) References Cited

U.S. PATENT DOCUMENTS

| | | | | |
|---|---|---|---|---|
| 4,188,949 | A * | 2/1980 | Antoshkiw | A61M 3/005<br>604/199 |
| 4,655,747 | A | 4/1987 | Allen, Jr. | |
| 4,931,040 | A | 6/1990 | Haber et al. | |
| 5,630,800 | A * | 5/1997 | Blank | A61M 5/31596<br>604/82 |
| 5,788,670 | A | 8/1998 | Reinhard et al. | |
| 6,132,400 | A | 10/2000 | Waldenburg | |
| 7,048,720 | B1 | 5/2006 | Thorne, Jr. et al. | |
| 9,950,114 | B2 | 4/2018 | Thorne, Jr. et al. | |
| 10,322,235 | B2 | 6/2019 | Thorne, Jr. et al. | |
| 10,537,686 | B2 | 1/2020 | Mirabito et al. | |
| 10,549,050 | B2 | 2/2020 | Zivkovic et al. | |
| 2002/0035351 | A1 | 3/2002 | Lodice | |
| 2004/0122359 | A1* | 6/2004 | Wenz | B01F 35/713<br>604/82 |
| 2007/0217282 | A1* | 9/2007 | Lidgren | B01F 33/50112<br>366/195 |
| 2009/0018496 | A1 | 1/2009 | Harper et al. | |
| 2010/0228121 | A1 | 9/2010 | Kazuhiro et al. | |
| 2012/0197232 | A1 | 8/2012 | Lee et al. | |
| 2016/0030708 | A1 | 2/2016 | Casiello et al. | |
| 2016/0279341 | A1* | 9/2016 | Anderson | A61M 5/31596 |
| 2017/0043094 | A1 | 2/2017 | Johansen et al. | |
| 2022/0134003 | A1 | 5/2022 | Rivier et al. | |

OTHER PUBLICATIONS

PCT International Search Report and Written Opinion in PCT/US2023/081544 dated Mar. 22, 2024, 16 pages.

* cited by examiner

DUAL CHAMBER SYRINGE WITH MANUALLY ACTUATED, CHAMBER ISOLATION VALVE

CROSS-REFERENCE TO RELATED APPLICATIONS

This application incorporates by reference in their entirety the following United States utility patent applications: entitled "SYRINGE WITH CONCENTRIC DUAL CHAMBERS", filed contemporaneously herewith on Nov. 30, 2022 and assigned U.S. Ser. No. 18/071,893, and "SYRINGE WITH TANDEM DUAL CHAMBERS", filed contemporaneously herewith on Nov. 30, 2022 and assigned U.S. Ser. No. 18/071,897.

TECHNICAL FIELD

The present disclosure generally relates to a dual chamber syringe assembly for administering two gases or fluids, or for administering and flushing catheters and other vascular accessing devices (VADs), or for mixing and administering fluids, and methods of flushing a catheter.

BACKGROUND

VADs are commonly used therapeutic devices and include I.V. catheters. There are two general classifications of VADs: peripheral catheters and central venous catheters. If not properly maintained, VADs can become occluded. To ensure VADs are used properly and do not become occluded, standards of practice have been developed. These standards include a cleaning procedure, which is commonly referred to as a flush procedure or flushing a catheter.

VAD standards of practice usually recommend flush procedures be performed after catheter placement, before fluid infusion, and before and after drug administration, blood sampling, transfusions, and parenteral nutrition. The goal of these flush procedures is to confirm catheter patency, avoid drug incompatibilities, ensure the complete drug dose administration, prevent thrombus formation, and minimize the risk of blood stream infections. Flush procedures require several types and amounts of flush solutions. Commonly used flush solutions are saline and/or heparin lock solution. The type of flush solution and amount vary depending on the specific type of catheter. Flush solution volumes between 5 and 10 ml are most common but can range from 1 ml to 20 ml.

For flush procedures, an I. V. line refers to a system containing a VAD, a tubing set with clamp and may terminate with a port or valve. The most common types of ports are covered by pierceable septums or pre-slit septums and are known in the art and sometimes referred to as "PRN" from the Latin pro re nata meaning "as the need arises". The septum is preferably made of rubber or another elastomeric material, which permits insertion of a sharp needle cannula to infuse fluids or to withdraw fluids from the catheter. Upon withdrawal of the needle cannula the septum seals itself. Ports having pre-slit septums are used with blunt cannula or the frusto-conically shaped tip of a syringe barrel. The syringe tip or the blunt cannula (which is usually attached to a syringe) is gently pushed through the pre-slit septum to establish fluid communication.

I.V. valves, another type of terminal I.V. access device that does not require a needle having a sharp tip, are activated by the frusto-conically shaped tip of a syringe barrel to allow fluid communication between the interior of the syringe and the catheter. These valves may contain structure for delivering fluid from a storage compartment in the valve to the catheter and are referred to in the art as positive displacement valves.

The removal of debris or residue is referred to as "purging" or "flushing" and prevents the build-up of deposits of blood, blood residue and IV drugs within a catheter or other VAD device. Such build-up can cause partial or complete blockage of the fluid pathway in a catheter system and can also require expensive and potentially dangerous methods for purging the affected catheter or a total catheter exchange. Often, such blockages lead to interruptions in therapy that may compromise patient care. The build-up of residue within a catheter can also increase infection risk by providing a breeding medium for microorganisms.

As is understood by one skilled in the art, flushing techniques involve injecting a flush solution, e.g., a saline solution, into VADs to clear debris and blockage. Injection is commonly done by a advancing a plunger rod into a pre-filled syringe barrel thereby expelling the flush solution into the VAD. When such techniques are used in conjunction with catheters, turbulence is introduced within the catheter, moving any debris or residue attached to the catheter. Flushing techniques require the application of substantially constant pressure or force to the plunger rod in the distal direction. Conventional or smooth flushing techniques may also include the application of pressure or force that increases or decreases substantially linearly to the plunger rod in the distal direction.

After flushing, the practitioner is then able to administer a dosage of medical fluid, the fluid being in a vial which requires withdrawal therefrom, or in a separate pre-filled syringe. However, the connecting of multiple devices to a VAD introduces the connectors to an unsterile outside environment, thereby introducing the possibility of transmitting a catheter related bloodstream infection (CRBSI), which can be costly and potentially lethal. To decrease CRBSI cases and to ensure VAD's are used and maintained correctly, standards of practice have been developed, which include disinfecting and cleaning procedures.

Administration of intravenous medication followed by IV flush, typically utilize two separate syringes in clinical practice.

There is a need for a syringe assembly which has the means to both flush a VAD and administer a dosage of medical fluid, thereby reducing the risk of CRBSI. There is also a need for a single syringe for administration of intravenous medication followed by IV flush, to increase clinician efficiency, and reduce costs associated with maintaining syringe inventory, and medical waste disposal.

SUMMARY

A dual chamber syringe facilitates selective drug mixing, dosing, and administration through catheters or other vascular accessing devices (VADs), as well as pre- or post-administration flushing of catheters with a single syringe instrument. A syringe barrel incorporates an outlet, such as a Luer connector, primary and secondary, variable-volume fluid chambers, with nested respective plungers, plunger rods capable of selective translation within the barrel interior along a common axis, and plunger stoppers. An externally accessible, selectively resealable, manual valve disposed within the barrel interior, selectively isolates the secondary fluid chamber from fluid communication with the primary fluid chamber and the outlet of the syringe barrel. Selective manipulation of the valve facilitates aspiration into or discharge from either of the chambers separately or jointly. The isolated, secondary chamber construction advantageously facilitates use of pre-packaged drugs or flushing solutions in that chamber. Use of syringes of the type disclosed herein, in medical procedures requiring both flushing and administration of drugs through catheters or other VADs, reduces the need to perform multiple infusions and withdrawals of multiple, single-function syringes. Use of the disclosed syringes advantageously reduces risk of patient infection, reduces costs associated with syringe inventory and subsequent waste disposal, and reduces clinician time necessary to complete the associated medical procedures.

One aspect of the present disclosure pertains to a syringe comprising substantially cylindrically shaped barrel, which defines an inner side wall, with the barrel having an open proximal end, and a distal end. The distal end of the barrel includes a connector, such as a Luer connector, which defines an outlet lumen therethrough that is in fluid communication with the interior of the barrel. The barrel interior is defined by the open proximal end, the distal end, and the inner side wall of the barrel. The syringe further comprises nested primary and secondary plungers, disposed within the barrel interior, respectively having primary and secondary plunger rods capable of selective translation within the barrel interior along a common axis. The primary plunger has a hollow tubular plunger rod. A primary stopper is coupled to a distal end of the primary plunger. It has a proximal end surface facing the proximal end of the barrel, a distal end surface facing the distal end of the barrel, and further defines a through aperture between its proximal and distal end surfaces, which is in fluid communication with the outlet lumen. A secondary stopper is coupled to a distal end of the secondary plunger; it has a distal end surface facing the distal end of the barrel. A rescalable valve is oriented within the tubular, primary plunger rod, axially offset, along the common axis, toward the distal end of the barrel away from the distal end surface of the secondary stopper. The rescalable valve has an inlet in fluid communication with the distal end surface of the secondary stopper and an outlet in fluid communication with the through aperture of the primary stopper and the outlet lumen. The rescalable valve has a spring-loaded, reciprocating needle aligned along the common axis, with the needle opening the valve in an open engagement position and the needle closing the valve in a closed engagement position. The syringe has a variable-volume, primary fluid chamber within the barrel interior, defined between the distal end surface of the primary stopper and the distal end of the barrel. Volume of the primary fluid chamber is selectively variable by translation of the primary plunger rod. The syringe also has a variable-volume, secondary fluid chamber, within the barrel interior, defined between the distal end surface of the secondary stopper and the valve inlet. The secondary fluid chamber is in fluid communication with the valve inlet. Volume of the secondary fluid chamber is selectively variable by translation of the secondary plunger rod. When the valve is closed, the secondary fluid chamber is isolated from the outlet lumen, so that translation of the primary plunger rod only aspirates fluid into or dispenses fluid out of the primary chamber, via the outlet lumen. When the valve is open, the secondary fluid chamber is in fluid communication with the outlet lumen, so that translation of the secondary plunger rod aspirates fluid into or dispenses fluid out of the secondary chamber, via the outlet lumen.

In some embodiments of the syringe disclosed herein, its secondary chamber is pre-filled with flushing solution. Desirably, a clinician can administer a medication into a patient's VAD with the primary chamber and immediately flush the VAD with the second chamber, without removing the syringe from the VAD. In other embodiments of the syringe disclosed herein a clinician can administer medication through, and thereafter immediately flush, a VAD with a single, continuous advancement of both dual plungers.

Another aspect of the present disclosure pertains to a syringe comprising substantially cylindrically shaped barrel, which defines an inner side wall, with the barrel having an open proximal end, and a distal end. The distal end of the barrel includes a connector, such as a Luer connector, which defines an outlet lumen therethrough that is in fluid communication with the interior of the barrel. The barrel interior is defined by the open proximal end, the distal end, and the inner side wall of the barrel. The syringe further comprises nested primary and secondary plungers, disposed within the barrel interior, respectively having primary and secondary plunger rods capable of selective translation within the barrel interior along a common axis. The primary plunger has a hollow tubular plunger rod defining a cam slot with open and closed engagement surface portions. A primary stopper is coupled to a distal end of the primary plunger. It has a proximal end surface facing the proximal end of the barrel, a distal end surface facing the distal end of the barrel, and further defines a through aperture between its proximal and distal end surfaces, which is in fluid communication with the outlet lumen. A secondary stopper is coupled to a distal end of the secondary plunger; it has a distal end surface facing the distal end of the barrel. A rescalable valve is oriented within the tubular, primary plunger rod, axially offset, along the common axis, toward the distal end of the barrel away from the distal end surface of the secondary stopper. The resealable valve has an inlet in fluid communication with the distal end surface of the secondary stopper and an outlet in fluid communication with the through aperture of the primary stopper and the outlet lumen. The rescalable valve has a spring-loaded, reciprocating needle aligned along the common axis, with the needle opening the valve in an open engagement position and the needle closing the valve in a closed engagement position, with a radially projecting cross-pin retained with the cam slot. A tip of the needle abuts a valve seat formed in the proximal end surface of the primary stopper when the cross pin is oriented in the closed engagement surface portion of the cam slot and the needle tip is axially spaced away from valve seat when the cross pin is oriented in the open engagement surface portion. The syringe has a variable-volume, primary fluid chamber within the barrel interior, defined between the distal end surface of the primary stopper and the distal end of the barrel. Volume of the primary fluid chamber is selectively variable by translation of the primary plunger rod. The syringe also has a variable-volume, secondary fluid chamber, within the barrel interior, defined between the distal end surface of the secondary stopper and the valve inlet. The secondary fluid chamber is in fluid communication with the valve inlet. Volume of the secondary fluid chamber is selectively variable by translation of the secondary plunger rod. When the valve is closed, the secondary fluid chamber is isolated from the outlet lumen, so that translation of the primary plunger rod only aspirates fluid into or dispenses fluid out of the primary chamber, via the outlet lumen. When the valve is open, the secondary fluid chamber is in fluid communication with the outlet lumen, so that translation of the secondary plunger rod aspirates fluid into or dispenses fluid out of the secondary chamber, via the outlet lumen.

The respective features of the aspects and exemplary embodiments of the disclosure that are described herein may be applied jointly or severally in any combination or sub-combination.

BRIEF DESCRIPTION OF THE DRAWINGS

Exemplary embodiments of the disclosure are further described in the following detailed description in conjunction with the accompanying drawings, in which.

To facilitate understanding, identical reference numerals have been used, where possible, to designate identical elements that are common to the figures. The figures are not drawn to scale.

DETAILED DESCRIPTION

Figure 1:
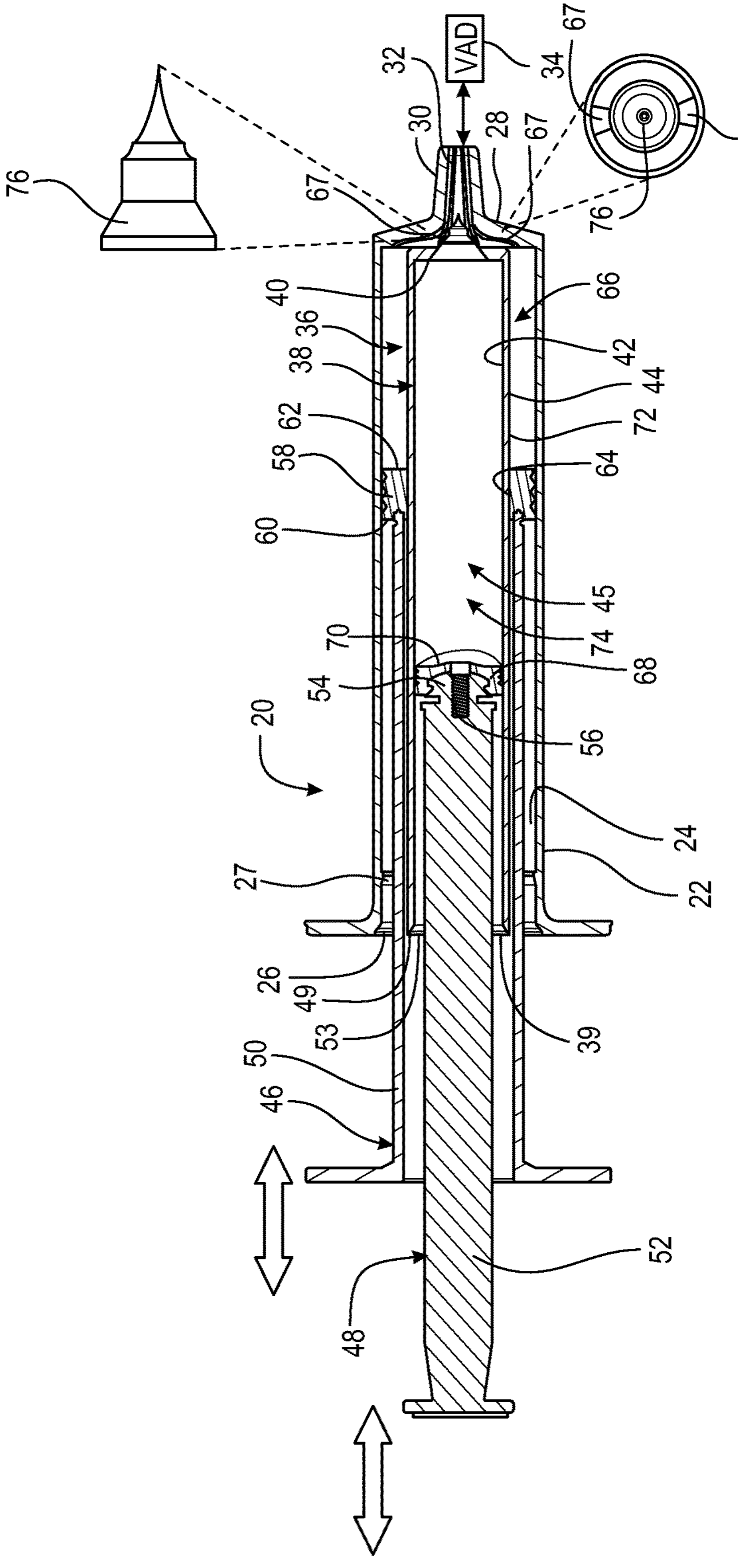
FIG. 1 is a cross-sectional view of an embodiment of a dual chamber syringe, with concentrically oriented primary and secondary fluid chambers, where each chamber contains fluid.
Figure 2:
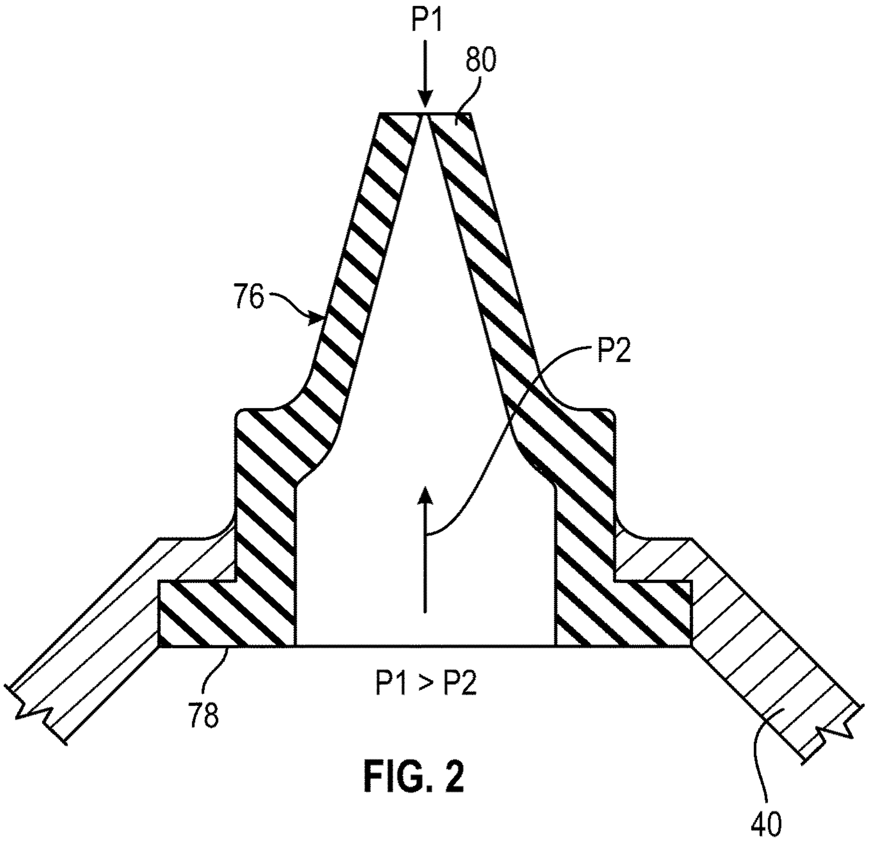
FIG. 2 is a cross-sectional view of a one-way, duckbill-type valve in a sealed or closed state.

Aspects of the dual chamber syringe embodiments disclosed herein facilitate selective drug mixing, dosing, and administration through catheters or other vascular accessing devices (VADs), as well as pre- or post-administration flushing of catheters with a single syringe instrument. Generally, in each disclosed embodiment, a syringe barrel incorporates an outlet, such as a Luer connector, in selective fluid communication with primary and secondary, variable-volume fluid chambers. In some embodiments, the chamber pair has tandem, in-line orientation within the syringe barrel, while in other embodiments, the chamber pair is nested in a generally concentric orientation. In either type of chamber orientation, the syringe incorporates, for each chamber, nested respective plungers, plunger rods capable of selective translation within the barrel interior along a common axis, and plunger stoppers. Thus, separate drugs or other fluids (e.g., flushing solution) are selectively and independently dispensed by the clinician. An externally accessible, selectively resealable, manual valve disposed within the barrel interior, selectively isolates the secondary fluid chamber from fluid communication with the primary fluid chamber and the outlet of the syringe barrel. Selective manipulation of the valve facilitates aspiration into or discharge from either of the chambers separately or jointly.

The isolated, secondary chamber construction advantageously facilitates use of pre-packaged drugs or flushing solutions in that chamber, whereby a clinician can aspirate and dispense medication with the empty primary chamber and thereafter immediately deliver pre-packaged flushing solution from the secondary chamber. In other embodiments, the syringe disclosed herein is used as a drug mixing syringe, prepackaged with a powdered drug in the primary chamber and a diluent solution in the secondary chamber. In some embodiments, a single advancing stroke on the nested, primary and secondary plungers of the syringe automatically delivers or infuses, sequentially into the VAD, a drug contained in the primary chamber, followed by flushing solution.

In this disclosure, a convention is followed wherein the distal end of the device is the end closest to a patient, e.g., for delivery of one or more drugs to the patient, and the proximal end of the device is the end away from the patient and closest to a clinician or other medical practitioner. With respect to terms used in this disclosure, the following definitions are provided.

As used herein, the use of "a," "an," and "the" includes the singular and plural.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is associated with a flush syringe and can interlock and connect to the female end located on the vascular access device (VAD). A Luer connector also has a distal end channel that releasably attaches the Luer connector to the hub of a VAD, and a proximal end channel that relcasably attaches the Luer connector to the barrel of a syringe.

As used herein, ISO 80369-7:2016 defines a specification for standard Luer connectors including a 6% taper between the distal end and the proximal end. A male standard Luer connector increases from the open distal end to the proximal end. A female standard Luer connector decreases from the open proximal end to the distal end. According to ISO 80369-7:2016, a male standard Luer connector has an outer cross-sectional diameter measured 0.75 mm from the distal end of the tip of between 3.970 mm and 4.072 mm. The length of the male standard Luer taper is between 7.500 mm to 10.500 mm. The outer cross-sectional diameter measured 7.500 mm from the distal end of the tip is between 4.376 mm and 4.476 mm. As used herein, the phrases "male standard Luer connector" and "female standard Luer connector" shall refer to connectors having the dimensions described in ISO 80369-7, which is hereby incorporated by reference in its entirety.

As would be readily appreciated by skilled artisans in the relevant art, while descriptive terms such as “tip”. “hub”, “thread”, “protrusion/insert”, “tab”, “slope”, “wall”, “top”, “side”, “bottom” and others are used throughout this specification to facilitate understanding, it is not intended to limit any components that can be used in combinations or individually or to require specific spatial orientations, to implement various aspects of the embodiments of the present disclosure.

Before describing several exemplary embodiments of the disclosure, it is to be understood that the disclosure is not limited to the details of construction or process steps set forth in the following description. The disclosure is capable of other embodiments and of being practiced or being conducted in many ways.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

In an exemplary implementation of the embodiments of present disclosure, a barrel of a syringe includes a distal end having a needleless connection. In one or more embodiments, the needleless connection includes at least one thread and other features in all combinations allowing it to interface with a corresponding thread or plurality of threads of a corresponding connector.

According to further exemplary implementations of the embodiments of the present disclosure, configuration of structural elements making up the needleless connector include a collar protruding from the distal end of the barrel, the collar comprising at least one thread to connect to the corresponding thread or plurality of threads of a corresponding connector.

According to still further exemplary implementations of the embodiments of the present disclosure, the collar or the needleless connector may bend or elastically deform to allow better interference fit compliance with corresponding connectors.

According to still further exemplary implementations of the embodiments of the present disclosure, the needleless connector may comprise female threads that are sized and have a thread pattern that will engage with a standard ISO594-2 type of male fitting and/or male threads that are sized and have a thread pattern that will engage with a standard ISO594-2 type of female fitting. An example of an ISO594-2 type of fitting is a Q-style fitting.

In one or more embodiments, a female connector may be selected from the group consisting essentially of: needle-type connectors (for direct injection into a patient or insertion into a drug vial for aspiration of a drug dose therefrom), needle-free connectors, catheter Luer connectors, stopcocks, and hemodialysis connectors. In one or more embodiments, the needleless connector is selected from a Q-Syte connector, MaxPlus, MaxPlus Clear, MaxZero, UltraSite, Caresite, In Vision-Plus, Safeline, OneLink, V-Link, ClearLink, NeutraClear, Clave, MicroClave, MicroClave Clear, Neutron, NanoClave, Kendall, *Nexus*, In Vision, Vadsite, Bionector, etc.

In one or more embodiments, the male connector may be an intravenous tubing end or a stopcock.

Referring now to the drawings, a first aspect of the present disclosure is shown in FIGS. 1-7, wherein a syringe 20 has concentrically oriented dual chambers. The syringe 20 comprises a substantially cylindrically shaped outer barrel 22, which defines an inner side wall 24, an open proximal end 26, an inwardly radially projecting plunger stop 27, and a distal end 28. The distal end 28 of the outer barrel 22 includes a Luer connector 30 defining an outlet lumen 32, for attachment to and fluid communication with various associated VAD connectors (shown schematically as connector 34). The interior 36 of the outer barrel 22 is generally defined and bounded by its inner side wall 24, open proximal end 26, and its distal end 28. The syringe 20 has an inner barrel 38 that is nested within the outer barrel 22 in radially spaced relationship. The inner barrel 38 has an open proximal end 39 and a distal tip 40 proximate the distal end 28 of the outer barrel 22. The inner barrel 38 has respective inner 42 and outer 44 side walls. The interior 45 of the inner barrel 38 is generally defined and bounded by its inner side wall 42, its open proximal end 39, and its distal tip 40.

The syringe 20 has nested primary 46 and secondary 48 plungers, respectively having primary 50 and secondary 52 plunger rods capable of selective translation along a common axis, within the interior 36 of the outer barrel 22. As shown in FIG. 1, primary plunger rod 50 has a tubular construction, integral with the primary plunger 46. The primary plunger 46 is nested within the outer barrel 22 and circumscribes the inner barrel 38. The secondary plunger 48 is in turn nested within the inner barrel 38 and the primary plunger 46. The secondary plunger rod 52 is selectively attached to an inner plunger head 54 of the secondary plunger 48 by screw 56, where male threads of the screw engage mating female threads formed in the secondary plunger rod.

An annular-shaped, primary stopper 58 is coupled to a distal end of the primary plunger 46. The primary stopper 58 has a proximal end surface 60 facing the proximal end 26 of the outer barrel 22, along with a distal end surface 62 facing the distal end 28 of the outer barrel. The primary stopper 58 is in fluid communication with the outlet lumen 32. The inner diameter 64 of the annular-shaped primary stopper 58 is in fluid sealing contact with the outer side wall 44 of the inner barrel 38 and defines a through aperture between its proximal 60 and distal 62 end surfaces. A variable volume, annular-shaped, primary chamber 66, also referred to as a primary cavity, is in fluid communication with the outlet lumen 32, via channels 67. However, when the primary stopper 58 is fully advanced into the outer barrel 22, its distal end surface 62 abuts a mating seating surface on that barrel's distal end 28, thereby isolating the primary chamber 66 from the channels 67 and the outlet lumen 32. Annular shape of the primary chamber 66 is defined within the boundaries of the distal end surface 62 of the primary stopper 58, the distal end 28 of the outer barrel 22, the inner side wall 24 of the outer barrel 22, and the outer side wall 44 of the inner barrel 38. Translation of the primary plunger rod 50 varies volume of the primary chamber 66. Withdrawal or retraction of the primary plunger rod 50 aspirates fluid from the outlet lumen 32 into the primary chamber 66. Retraction of the primary plunger rod 50 is limited by contact with the internal stop 27 formed in the outer barrel 22. Conversely, insertion or advancement of the primary plunger rod 50 displaces and discharges fluid out of the primary chamber 66, through the outlet lumen 32. It follows that a clinician can selectively aspirate or discharge fluid, such as drugs or flushing solution into or out of the primary chamber 66 of the syringe 20.

A secondary stopper 68 is coupled to an inner plunger head 54 at the distal end of the secondary plunger 48. An end cap 53 is coupled to the proximal, open side of the inner barrel 38, to prevent inadvertent dislodging or separation of the inner plunger head 54 and the secondary stopper 68 out of the inner barrel. The secondary stopper has a distal end surface 70 facing the distal tip 40 of the inner barrel 38 and the distal end 28 of the outer barrel 22 and an outer circumferential surface 72 that is in fluid sealing contact with the inner side wall 42 of the inner barrel 38. A variable volume, secondary chamber 74, also referred to as a secondary cavity, is defined within the boundaries of the distal end surface 70 of the secondary stopper 68, and the distal tip 40 and inner side wall 42 of the inner barrel 38. Translation of the secondary plunger rod 52 varies volume of the secondary chamber 74. It follows that a clinician can selectively discharge fluid, such as drugs or flushing solution out of the secondary chamber 74 by advancing the secondary plunger rod 52 into the syringe 20. In some embodiments, when the syringe 20 is pre-packaged with fluid in the secondary chamber 74, the secondary plunger rod 52 is intentionally detached from the secondary plunger 48, to prevent inadvertent dosing. A clinician attaches the secondary plunger rod 52 prior to administering the pre-packaged dose to a patient.

Figure 3:
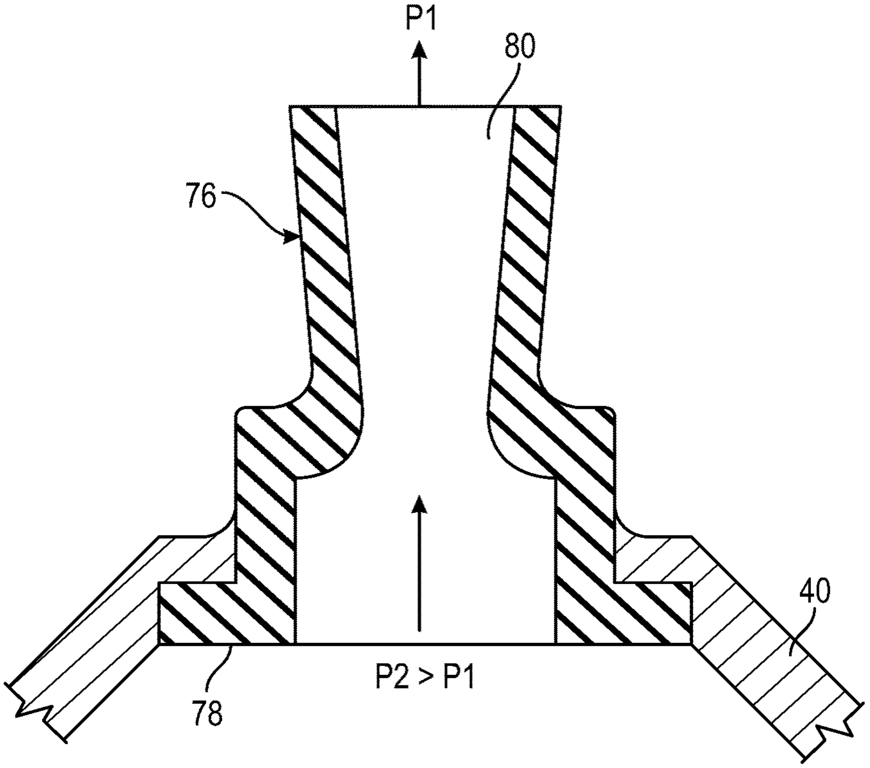
FIG. 3 is a cross-sectional view of the one-way, duckbill-type valve of FIG. 2 in an open state.

The syringe 20 embodiment of FIGS. 1-7 incorporates a one-way valve 76, coupled to the distal tip 40 of the inner barrel 38, for selective isolation of the secondary chamber 74 from the outlet lumen 32 of the Luer connector 30. When the syringe 20 is in use, clinician can discharge fluid from the secondary chamber 74 out of the outlet lumen 32 by advancing the secondary plunger rod 52 into the inner barrel 38 but cannot aspirate fluid into the secondary chamber. Hence, the one-way valve 76 functions as a check valve. Physical structure and operation of the one-way valve 76 is shown schematically in FIGS. 2 and 3. The one-way valve 76 is a duckbill-type valve, constructed of monolithic elastomer (e.g., medical grade silicone) in a conical or frustoconical profile. An inlet 78 of the duckbill valve 76 is coupled to the distal tip 40 of the inner barrel 38, while its outlet 80 is oriented to face the Luer connector 30. As shown in FIG. 3, the outlet 80 is in a sealed, relaxed state when pressure P1 in the Luer Connector 30 is greater than or equal to the pressure P2 in the secondary chamber 74. Conversely, in FIG. 3, when pressure P2 is greater than pressure P1, such as when the secondary plunger 48 is advanced into the syringe 20, the elastomer in the valve 76 stretches and deforms radially outwardly, discharging fluid from the secondary chamber 74.

Figure 4:
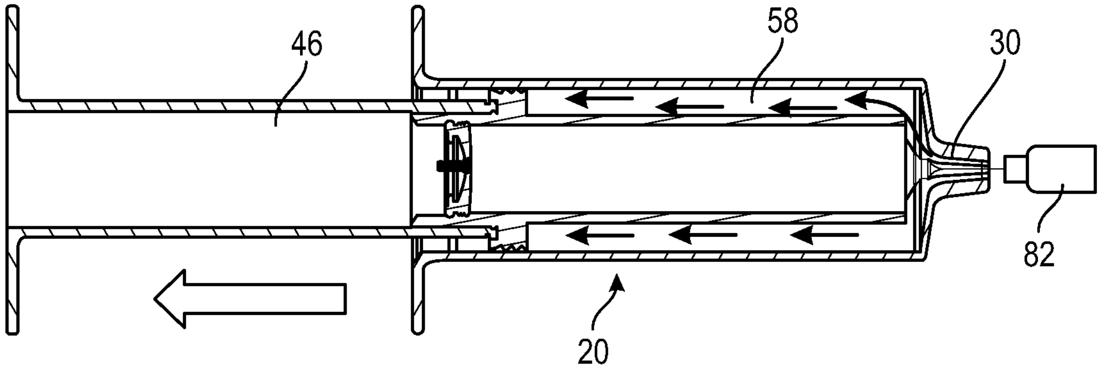
FIGS. 4-7 are illustrative, sequential steps, for use of the syringe of FIG. 1, respectively showing aspiration and dispensing/infusing of a fluid in the primary chamber, such as a drug, into an intravenous fluid catheter or port, followed by flushing the catheter with fluid in the secondary chamber.
Figure 5:
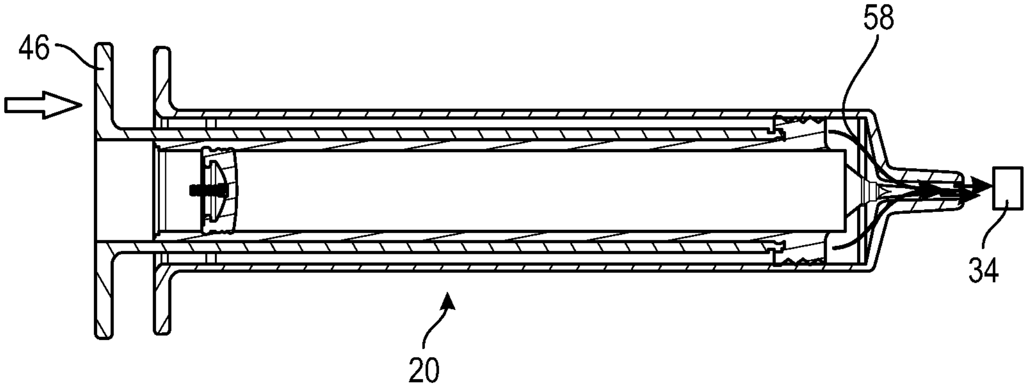
Figure 6:
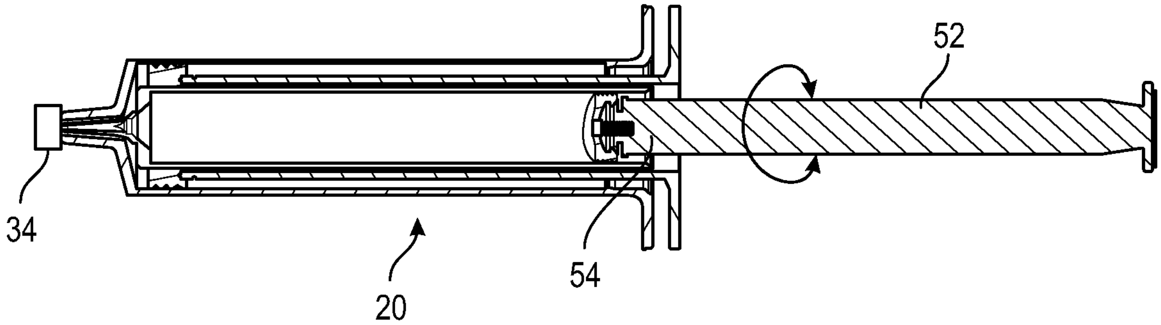
Figure 7:
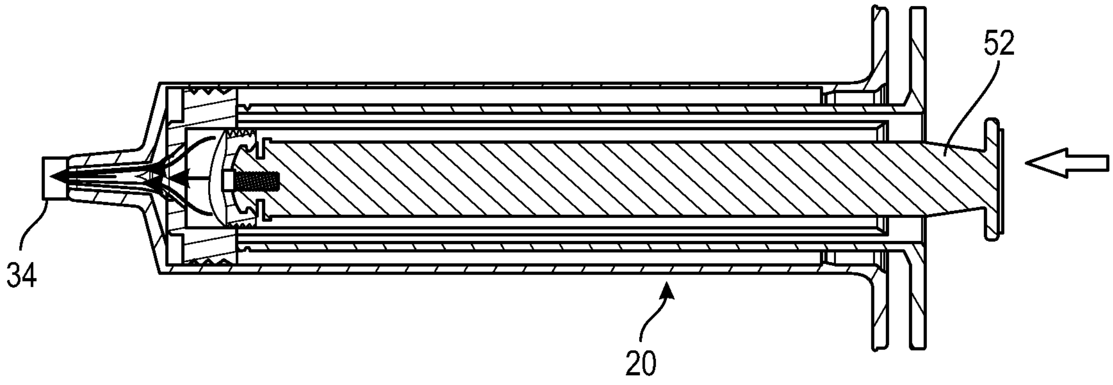
Figure 8:
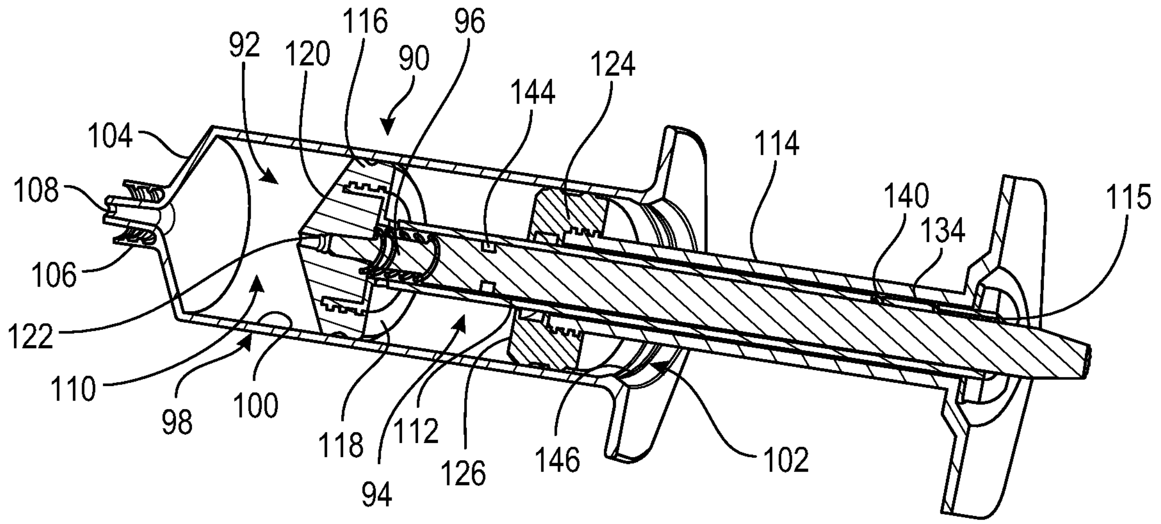
FIG. 8 is a cross-sectional view of another embodiment of a dual chamber syringe, which incorporates an externally actuated isolation valve, where each chamber contains fluid.
Figure 9:
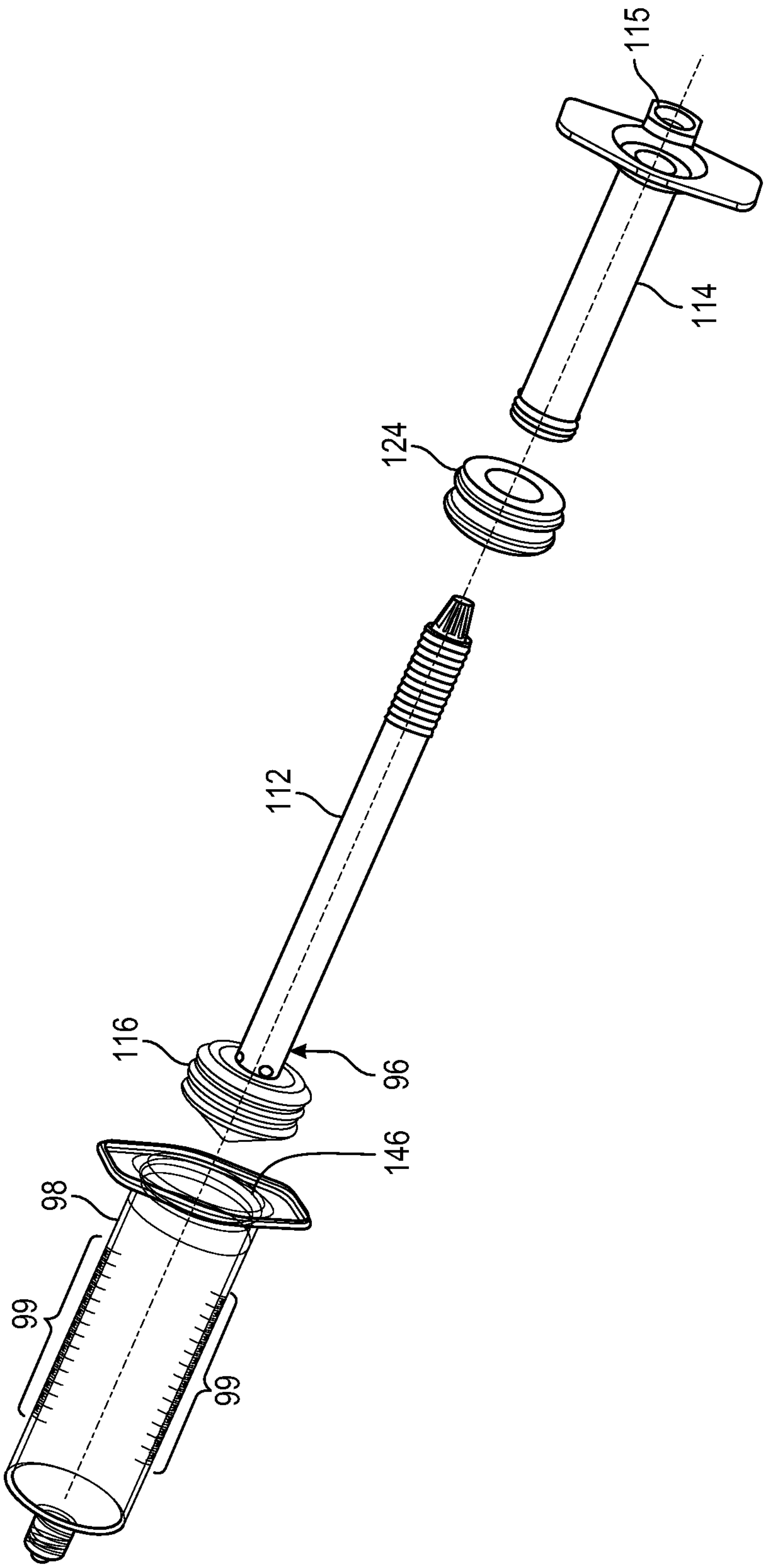
FIG. 9 is an exploded view of the syringe of FIG. 8.

FIGS. 4-7 depict functional operation of the syringe 20, by first withdrawing the primary plunger 46 to aspirate medication from a drug vial 84, via the Luer connection 30, into its primary chamber 66 (FIG. 4). The medication is infused from the primary chamber 66 into a previously flushed VAD 34, by advancing the primary plunger 46, thereby emptying the primary chamber (FIG. 5). If not previously affixed to the syringe 20, the secondary plunger rod 52 is affixed its corresponding inner plunger head 54 (FIG. 6). The VAD 34 is flushed with flushing solution (e.g., saline or heparin) pre-packaged in the secondary chamber 74 by advancing the secondary plunger rod 52. Upon completion of the flushing procedure, syringe 20 is then withdrawn from the VAD 34.

Another aspect of the present disclosure is shown in FIGS. 8-12, wherein a dual chamber syringe 90 has tandem, axially aligned and oriented, variable volume, primary 92 and secondary 94 chambers, with a manually actuated, selective isolation valve 96 that facilitates either aspiration into or discharge of fluid from its secondary chamber. In one or more embodiments, the primary chamber 92 is filled with a desired amount of a saline flush fluid. In one or more embodiments, the primary chamber 92 is filled with a desired medicine. In one or more embodiments, the secondary chamber 94 is filled with a desired amount of a saline flush fluid. In one or more embodiments, the secondary chamber 94 is filled with a desired medicine. In one or more embodiments, both the primary 92 and secondary 94 chambers are filled with a desired medicine. In one or more embodiments, both the primary 92 and secondary 94 chambers are filled with desired amounts of saline flush fluid. The primary chamber 92 and/or the secondary chamber 94 are pre-filled with fluid during or after the assembly of the syringe 90 using sterile filling methods. In addition, the barrel 98 of the syringe 90 may include measuring indicia 99 to indicate the amount of fluid contained within.

The syringe 90 comprises the substantially cylindrically shaped barrel 98, which defines an inner side wall 100. The barrel 98 has an open proximal end 102, and a distal end 104. The distal end 104 of the barrel 98 includes a Luer connector 106, defining an outlet lumen 108 therethrough. The outlet lumen 108 is in fluid communication with an interior 110 of the barrel 98, with the interior defined by the open proximal end 102, the distal end 104, and the inner side wall 100.

The syringe 90 comprises nested, primary 112 and secondary 114 plungers, disposed within the barrel interior 110, respectively having integral, tubular-shaped, primary, and secondary plunger rods capable of selective translation within the barrel interior along a common axis. A threaded plunger nut 115 mates with exterior threads formed on a distal end of the primary plunger 112, which also captures the secondary plunger 114 and maintains both plungers in nested orientation.

A primary stopper 116 is coupled to a distal end of the primary plunger 112. The primary stopper 116 has a proximal end surface 118 facing the open proximal end 102 of the barrel 98 and a distal end surface 120 facing the distal end 104 of the barrel. The primary stopper 116 defines a through aperture 122 between its proximal 118 and distal 120 end surfaces, in fluid communication with the outlet lumen 108. A secondary stopper 124 is coupled to a distal end of the secondary plunger 114. The secondary stopper has a distal end surface 126 facing the distal end 104 of the barrel 98.

Figure 10:
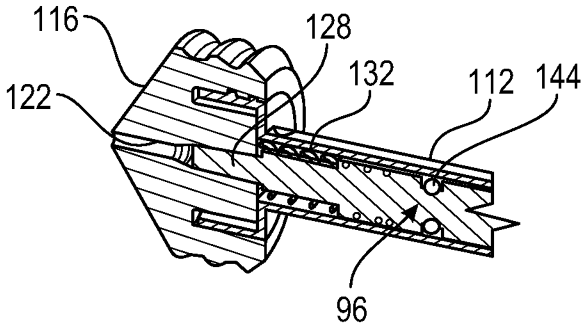
FIGS. 10 and 11 are detailed cross-sectional views of the syringe of FIG. 8, showing a needle valve respectively in closed and open positions.
Figure 11:
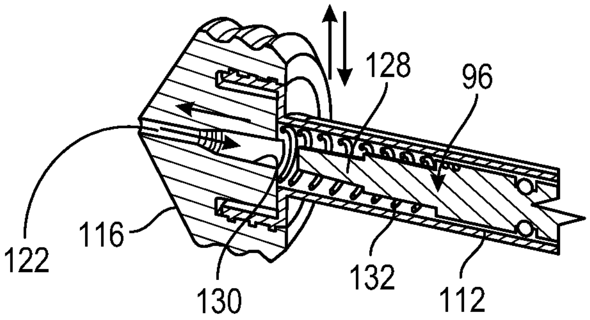
Figure 12:
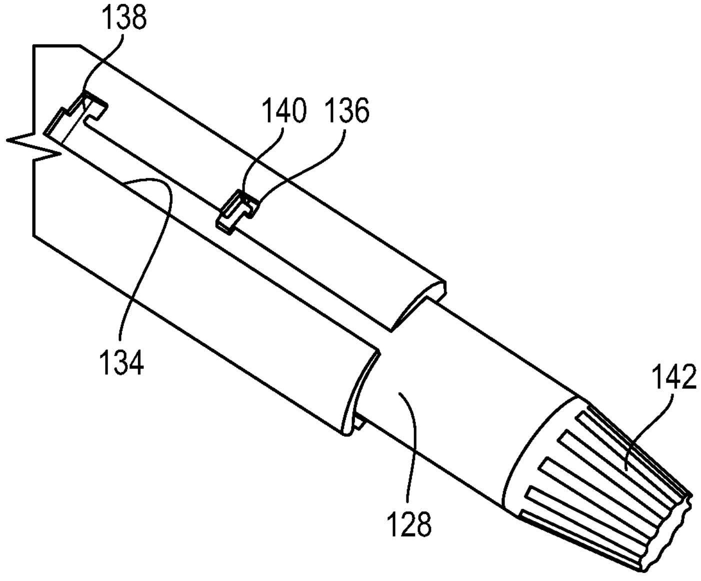
FIG. 12 is a perspective view of the syringe of FIG. 8, showing a cam slot for selectively engaging the needle valve in the closed and open positions of FIGS. 10 and 11.

Referring to FIGS. 10-12, the isolation valve 96 comprises a spring loaded, shaft-mounted needle valve 128 disposed in the tubular, primary plunger 112 and a mating seat 130 formed in the through aperture 122 of the primary stopper. In some embodiments, the needle valve 128 and seat 130 have Luer connector profiles. Spring 132 biases the needle valve 128 away from the seat 130, maintaining the isolation valve in an open position; this allows fluid flow from the secondary chamber 94 into the primary chamber 92 and the outlet 108. The primary plunger 112 defines at least one cam slot 134 with open 136 and closed 138 engagement surface portions, within which constrains a radially projecting cross pin 140 of the shaft of the needle valve 116. The isolation valve 96 is closed by twisting and then depressing the fluted knob 142 on the shaft of the needle valve 128 out of the open engagement surface 136 of the cam slot 134. This compresses the spring 132 and advances the needle valve 128 into mating contact with the corresponding seat 130, thereby closing the valve and isolating the secondary chamber 94 from the primary chamber 92 and the outlet 108 of the Luer connector 106. The needle valve 128 is locked in its closed position by twisting the fluted knob 142 so that the cross pin 140 of the isolation valve 96 is engaged and restrained within the closed engagement surface 138 of the cam slot 134. In some embodiments, the primary plunger 112 has three cam slots 134 and there are three corresponding cross pins 140 on the isolation valve 96. Annular shaft seal 144 inhibits fluid leaks between the elongated stem of the isolation valve 96 and the primary plunger 112. The primary plunger 112 and the shaft of the needle valve 128 are dimensioned to restrain buckling of the shaft and maintain perpendicular alignment of the needle valve tip and its mating seat 130.

When utilizing the syringe 90, the secondary chamber 94 is pre-filled with fluid, with the isolation valve 96 in the closed position to prevent leakage of the fluid. Alternatively, the secondary chamber 94 is filled on site at the treatment center. If the latter, prior to filling the syringe 90, the isolation valve 96 is opened; both the primary 116 and secondary 124 stoppers are fully advanced with the primary 112 and secondary 114 plungers, so that the distal end surface 120 of the primary stopper 116 abuts the distal end 104 of the barrel 98 and the distal end surface 126 of the secondary stopper 124 abuts the proximal end surface 118 of the primary stopper. Now, both primary 92 and secondary 94 chambers have been compressed to a zero-volume state. To aspirate and fill the empty secondary chamber 94, the secondary plunger 114 is retracted while the primary plunger remains in its fully advanced position. A plunger-stop 146 projects radially into the interior of the barrel 98, to prevent inadvertent separation of the primary 112 and secondary 114 plungers from the barrel. The isolation valve 96 is closed when the secondary chamber 94 is filled to desired capacity, isolating its contents. Thereafter, the primary chamber 92 is aspirated by retracting the primary plunger 112. In some applications the syringe 90 is utilized to reconstitute a powdered medicine that has been prefilled in the primary chamber 92, by dispersing pre-filled diluent liquid stored in the secondary chamber 94 into the primary chamber. In other applications, a drug is aspirated and dispensed into a VAD with the primary chamber 92 and subsequently the VAD is flushed with a flushing solution stored in the secondary chamber 94, after opening the isolation valve 96.

Another aspect of the present disclosure is shown in FIGS. 13-16, wherein a dual chamber syringe 150 has tandem, axially aligned and oriented, variable volume, primary 152 and secondary 154 chambers. The secondary chamber 154 is incorporated within a primary plunger 172. A one-way, duckbill-type valve 156 facilitates discharge of fluid from its secondary chamber 154. The duckbill valve 156 has similar construction and operation as the duckbill valve 76 of FIGS. 2 and 3; it does not allow backflow or reflux of fluid into the secondary chamber 154. As with the previously described syringe embodiments, in one or more embodiments of the syringe 150, the primary chamber 152 and/or the secondary chamber 154 are separately pre-filled with one or more fluids, such as flush fluid or medicine.

The syringe 150 comprises the substantially cylindrically shaped barrel 158, which defines an inner side wall 160. The barrel 158 has an open proximal end 162, and a distal end 164. The distal end 164 of the barrel 158 includes a Luer connector 166, defining an outlet lumen 168 therethrough. The outlet lumen 168 is in fluid communication with an interior 170 of the barrel 158, with the interior defined by the open proximal end 162, the distal end 164, and the inner side wall 160.

The syringe 150 comprises nested, primary 172 and secondary 174 plungers, disposed within the barrel interior 170, respectively having integral, primary and secondary plunger rods capable of selective translation within the barrel interior 170 along a common axis. The primary plunger 172 has hollow tubular construction and incorporates the structure of the secondary chamber 154. Thus, the secondary chamber 154 translates with the primary plunger 172 when the latter is advanced or withdrawn within the barrel interior 170. In addition, the outer surfaces of the barrel 158 and/or the secondary plunger 174 may include measuring indicia to indicate the amount of fluid contained within.

Figure 13:
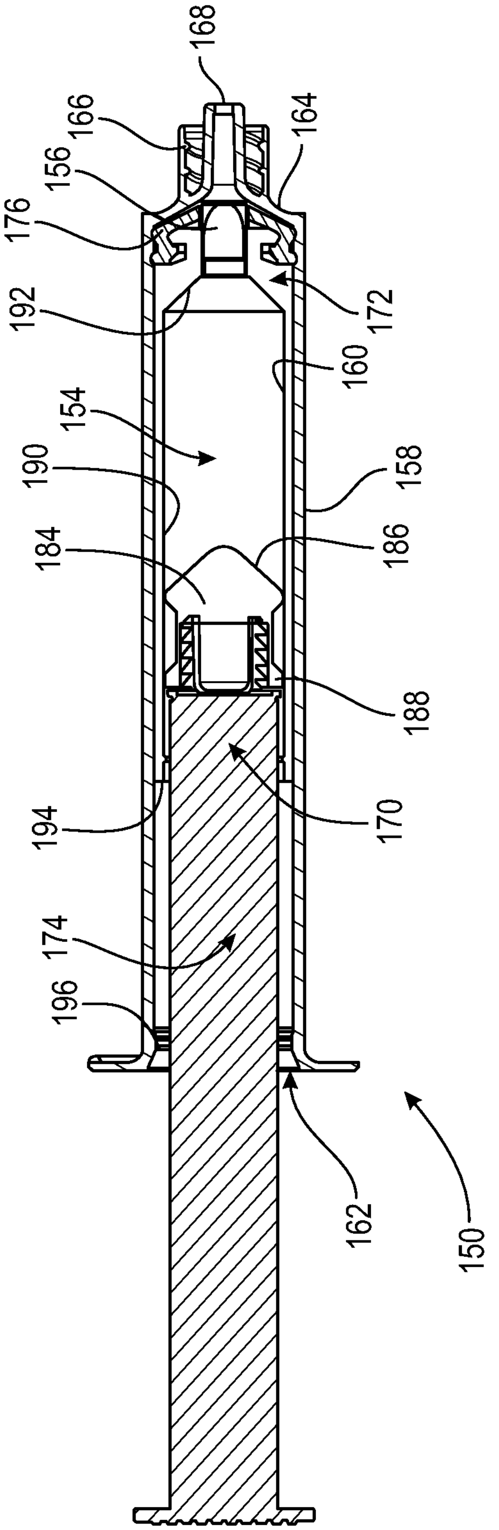
FIG. 13 is a cross-sectional view of another embodiment of a dual chamber syringe, where the secondary or proximal chamber is incorporated within the primary plunger thereof, and is pre-filled with fluid.
Figure 16:
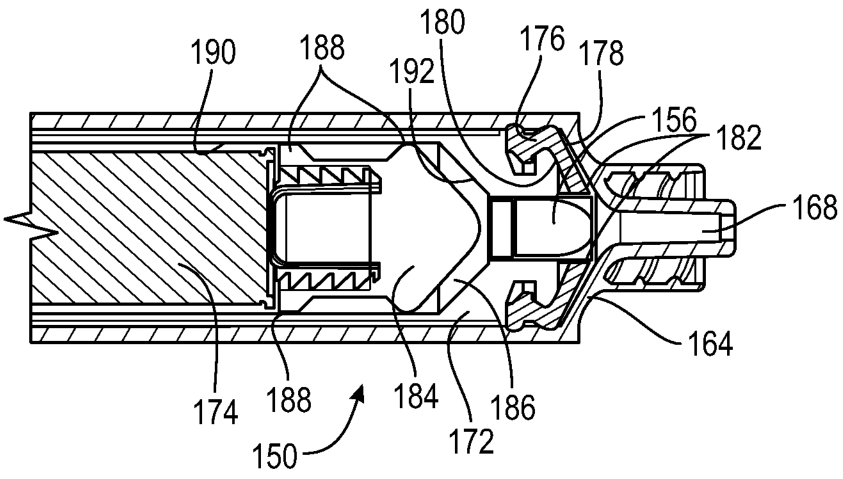
FIG. 16 is a cross-sectional view of the syringe of FIG. 13 after all fluid in the secondary or proximal chamber has been dispensed.

Referring to FIGS. 13 and 16, a primary stopper 176 is coupled to a distal end of the primary plunger 172. The primary stopper 176 has a proximal end surface 178 facing the open proximal end 162 of the barrel 158 and a distal end surface 180 facing the distal end 164 of the barrel. The primary stopper 176 defines a through aperture 182 between its proximal 178 and distal 180 end surfaces, with the aperture in fluid communication with the outlet lumen 168. A secondary stopper 184 is coupled to a distal end of the secondary plunger 174. The secondary stopper has a distal end surface 186 facing the distal end 164 of the barrel 158 and a circumferential sealing skirt 188. The circumferential sealing skirt 188 is in friction tight, fluid sealing contact with the inner side wall 190 of the primary plunger 172.

Figure 14:
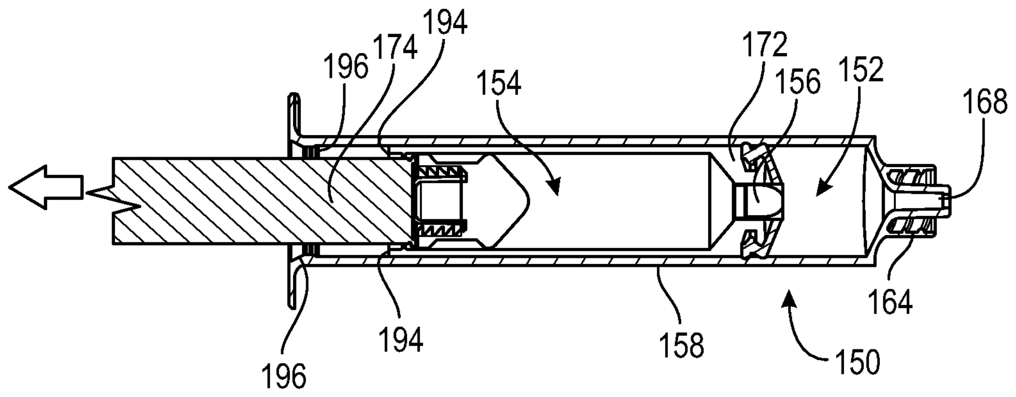
FIG. 14 is a cross-sectional view of the syringe of FIG. 13, where another fluid has been aspirated into a primary or distal chamber thereof.
Figure 15:
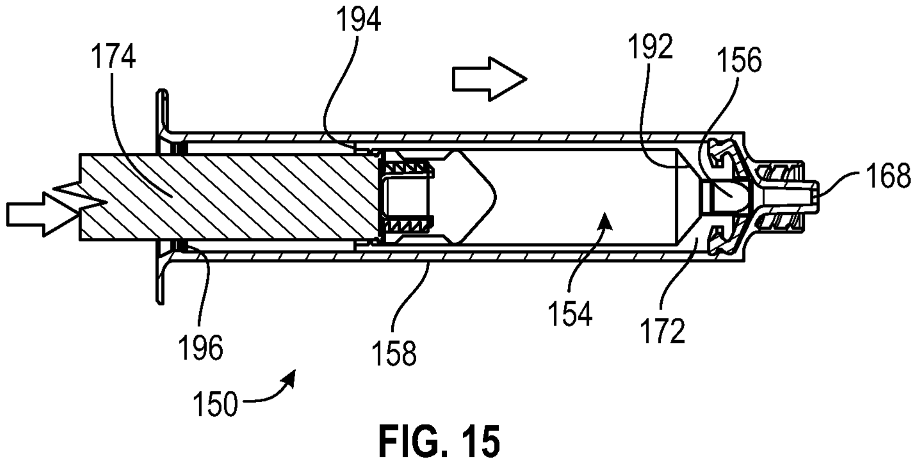
FIG. 15 is a cross-sectional view of the syringe of FIG. 13, where fluid in the secondary or proximal chamber is being dispensed.

The variable volume, primary chamber 152 is defined within the boundaries of the distal end surface 180 of the primary stopper 176, the distal end 164 and the inner side wall 160 of the barrel 158, and the distal end surface 186 of the secondary stopper 184. The variable volume, secondary chamber 154 is defined within the boundaries of the distal end surface 186 of the secondary stopper 184, the distal end 194 and the inner side wall 190 of the tubular primary plunger 172, and the distal end surface 186 of the secondary stopper 184. In operation, as shown in FIGS. 13-16, an empty primary chamber 152 is aspirated and filled with a desired fluid by retracting the secondary plunger 174 (FIG. 14). Friction contacts between the circumferential sealing skirt 188 of the secondary stopper 184 and the opposed, abutting inner side wall 190 of the primary plunger 172 translates the latter plunger and its primary stopper 176 toward the proximal open end 162 of the barrel 158. To prevent inadvertent separation of the primary plunger 172 and the nested secondary plunger 174 from the barrel 158, retraction of both plungers is limited stopped when a proximal end surface 194 of the primary plunger with an internal stop ring 196 inserted in the open proximal end 162 of the barrel 158. In FIG. 15, the fluid in the primary chamber 154 has been discharged by advancing the secondary plunger 172 with sufficient force necessary to advance the primary stopper 176 to contact with the distal end 164 of the barrel 158 but limiting the advancing force to a level below what is necessary to open the duckbill valve 156. When it is desired to discharge the contents of the secondary chamber 154, the secondary plunger 174 is advanced with sufficient force to open the duckbill valve 156, as was previously explained with respect to discharge of the secondary chamber 74 of the syringe 20 (see FIG. 4). Thus, with the syringe 158 embodiment, a clinician can automatically and sequentially deliver medication with the primary chamber 154 and then deliver flushing solution with the secondary chamber 154 by continuously advancing the secondary plunger 174 with sufficient force to open the duckbill valve 156, without changing syringes.

Figure 17:
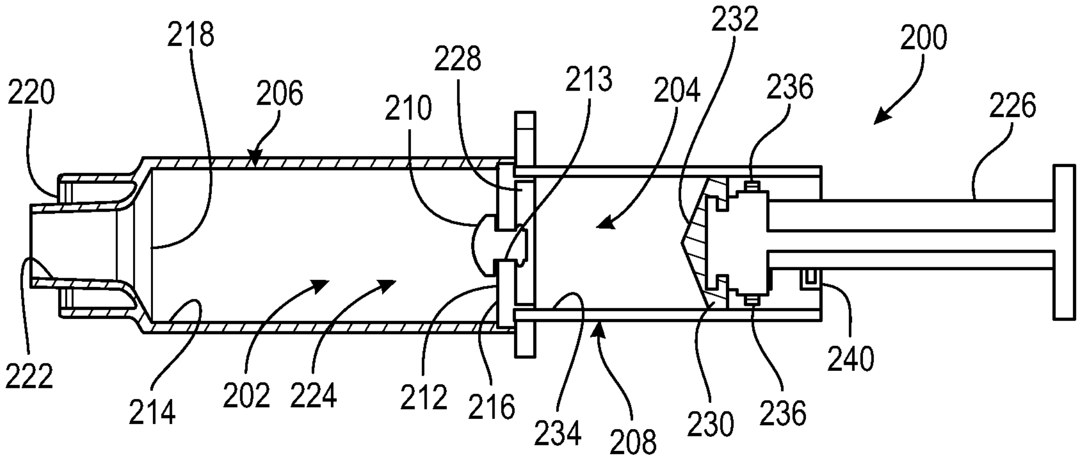
FIG. 17 is a cross-sectional view of another embodiment of a dual chamber syringe.

Another aspect of the present disclosure is shown in FIG. 17, wherein a dual chamber syringe 200 has tandem, axially aligned and oriented, variable volume, primary 202 and secondary 204 chambers formed in nested respective primary 206 and secondary 208 barrels. A one-way, umbrella valve 210 and mating umbrella valve seat 212 are coupled to the secondary barrel 208; they function as a primary stopper and facilitate storage in and discharge of fluid from the secondary chamber 204. The umbrella valve seat 212 defines a through aperture 213. The umbrella valve 210 is oriented within the through aperture 213, blocking fluid flow from the primary chamber 202 to the secondary chamber 204, which isolates the contents the secondary chamber from the rest of the syringe 200. As with the previously described syringe embodiments, in one or more embodiments of the syringe 200, the primary chamber 202 and/or the secondary chamber 204 are separately pre-filled with one or more fluids, such as flush fluid or medicine.

The substantially cylindrically shaped, primary barrel 206 defines an inner side wall 214, an open proximal end 216, and a distal end 218. The distal end 218 of the primary barrel 206 includes a Luer connector 220, defining an outlet lumen 222 therethrough. The outlet lumen 222 is in fluid communication with an interior 224 of the primary barrel 206, with the interior defined by the open proximal end 216, the distal end 218, and the inner side wall 214. The variable volume, primary chamber 202 is defined within the inner side wall 214, and the distal end 218 of the primary barrel 208 and the primary stopper comprising the umbrella valve 210/umbrella valve seat 212.

The syringe 200 comprises a nested, primary and secondary plunger pair that is capable of selective translation, along a common axis, within the interior 224 of the primary barrel 206. The secondary barrel 208 functions as an integrated, primary plunger/integral plunger rod that is disposed within the primary barrel's interior 224. It follows that the entire secondary chamber 204 translates with the secondary barrel as the latter is used as a primary plunger to vary volume of the primary chamber 202 within the primary barrel 206. A retention ring 228 proximate the open proximal end 216 of the primary barrel 206 limits withdrawal of the integrated secondary barrel/primary plunger 208, to prevent inadvertent separation of the secondary barrel from the syringe 200. The secondary plunger 226 incorporates an integral plunger rod that is capable of selective translation within the respective interiors of the primary barrel 206 and the secondary barrel 208. In addition, the outer surfaces of either the primary barrel 206 and/or the barrel 208 and/or the secondary plunger 226 may include measuring indicia to indicate the amount of fluid contained within.

A secondary stopper 230 is coupled to a distal end of the secondary plunger 226. The secondary stopper has a distal end surface 232 facing the distal end 218 of the primary barrel 208. The variable volume, secondary chamber 204 is defined within the boundaries of the distal end surface 232 of the secondary stopper 230, an inner side wall 234 of the secondary barrel 208, and the umbrella valve seat 212. A twist-lock mechanism, when in a locked state, selectively locks the secondary plunger 226 in its most retracted position relative to the secondary plunger barrel 208. so that advancement pressure on the secondary plunger only translates the secondary barrel 208 to vary selectively volume of the primary chamber 202. The twist-lock mechanism comprises s a pair of opposed, radially projecting lugs 336 formed on the secondary plunger 226 and mating corresponding lug recesses 240 formed within the inner side wall 234 of the secondary barrel 208. When the twist lock mechanism is in an unlocked state, the lugs 336 of the secondary plunger 226 are not engaged in the mating lug recesses 240 of the secondary barrel 208, allowing the secondary plunger and its attached secondary stopper 230 to translate within the secondary barrel.

The secondary chamber 204 of the syringe 200 is advantageously pre-filled with a desired fluid, such as water. In some embodiments, the primary chamber 202 is pre-filled with a dry powder drug that is subsequently mixed with diluent fluid from the secondary chamber 204 by unlocking the locking mechanism and advancing the secondary plunger 226. The mixed drug is infused into a VAD by locking the secondary plunger 226 with the locking mechanism and advancing it with the integrated, secondary barrel/208 primary plunger. In other embodiments, the secondary chamber 204 of the syringe 200 is provided pre-filled with a flushing solution and an empty primary chamber 202. The primary chamber 202 is selectively aspirated with a desired fluid, such as a drug, and discharged into a VAD. The VAD is subsequently flushed with the flushing solution in the secondary chamber 204 by use of the same syringe 200. Thus, with the syringe 200 embodiment, a clinician can automatically and sequentially deliver medication into and then flush the VAD by: (i) advancing the secondary plunger 226 while in a locked state, thereby discharging the drug-filled primary chamber 202 into the VAD, (ii) unlocking the secondary plunger with a simple twisting motion, and (iii) depressing the unlocked secondary plunger to discharge the flushing solution-filled secondary chamber 204 into the VAD, all without changing syringes.

The syringe embodiments disclosed herein are constructed from medical grade materials known to one skilled in the art. In some embodiments, described barrels, plungers and shafts are fabricated with polypropylene polymers. Seals are fabricated with fiber-filled polytetrafluoroethylene (PTFE) polymers. Stoppers are fabricated with polyisoprene polymers. Springs are fabricated with stainless steel.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments. In addition, it is to be understood that the phraseology and terminology used herein is for the purpose of description and should not be regarded as limiting. The use of "including," "comprising." or "having" and variations thereof herein is meant to encompass the items listed thereafter and equivalents thereof as well as additional items. Unless specified or limited otherwise, the terms "mounted." "connected." "supported," and "coupled" and variations thereof are to be interpreted broadly; they encompass direct and indirect mountings, connections, supports, and couplings. Further, "connected" and "coupled" are not restricted to physical, mechanical, or electrical connections or couplings.

Although the disclosure herein provided a description with reference to embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents. The appended claims are not limited to the exemplary embodiment details of construction and the arrangement of components set forth in the description or illustrated in the drawings.

What is claimed is:

1. A syringe comprising:

a substantially cylindrically shaped barrel which defines an inner side wall, the barrel having an open proximal end and a distal end, the distal end of the barrel including a connector defining an outlet lumen therethrough, the outlet lumen in fluid communication with an interior of the barrel, the interior defined by the open proximal end, the distal end, and the inner side wall;

nested primary and secondary plungers disposed within the barrel interior of the barrel, respectively having primary and secondary plunger rods capable of selective translation within the interior of the barrel along a common axis, the primary plunger rod being tubular;

a primary stopper coupled to a distal end of the primary plunger, the primary stopper having a proximal end surface facing the proximal end of the barrel and a distal end surface facing the distal end of the barrel, the primary stopper defining a through aperture between its proximal and distal end surfaces in fluid communication with the outlet lumen;

a secondary stopper coupled to a distal end of the secondary plunger, the secondary stopper having a distal end surface facing the distal end of the barrel;

a resealable valve formed by the primary stopper and a spring-loaded reciprocating needle aligned along the common axis, the through aperture of the primary stopper forming an outlet of the resealable valve and the primary plunger rod comprising an aperture forming an inlet to the resealable valve, the resealable valve oriented within the primary plunger rod of the primary plunger, along the common axis toward the distal end of the barrel away from the distal end surface of the secondary stopper, the reciprocating needle opening the valve in an open engagement position in which the distal end surface of the secondary stopper is in fluid communication with the through aperture of the primary stopper through the aperture of the primary plunger rod, the reciprocating needle closing the valve in a closed engagement position;

a primary fluid chamber within the interior of the barrel defined between the distal end surface of the primary stopper and the distal end of the barrel, a volume of the primary fluid chamber being selectively variable by translation of the primary plunger rod; and a secondary fluid chamber within the interior of the barrel defined between the distal end surface of the secondary stopper and the inlet to the valve and in fluid communication with the aperture of the primary plunger rod, a volume of the secondary fluid chamber being selectively variable by translation of the secondary plunger rod;

wherein, when the valve is closed, the secondary fluid chamber is isolated from the outlet lumen so that translation of the primary plunger rod only aspirates fluid into or dispenses fluid out of the primary fluid chamber via the outlet lumen; and wherein, when the valve is open, the secondary fluid chamber is in fluid communication with the outlet lumen so that translation of the secondary plunger rod aspirates fluid into or dispenses fluid out of the secondary fluid chamber via the outlet lumen.

2. The syringe of claim 1, wherein the secondary plunger is tubular and the primary plunger is nested in the secondary plunger; the secondary stopper having an annular cross-section with an outer diameter of the secondary stopper abutting the inner side wall of the barrel and an inner diameter thereof of the secondary stopper abutting an outer side wall of the tubular secondary plunger.

3. The syringe of claim 1, wherein an inner surface of the distal end of the barrel defines a seating surface for abutting engagement with the distal end surface of the primary stopper when the primary stopper is completely advanced within the barrel, thereby isolating the primary fluid chamber from the outlet lumen and the outlet of the valve.

4. The syringe of claim 3, wherein an inner surface of a distal end of the secondary fluid chamber defines a seating surface for abutting engagement with the distal end surface of the secondary stopper when the secondary stopper is completely advanced within the barrel, thereby isolating the secondary fluid chamber from the outlet lumen and the outlet of the valve.

5. The syringe of claim 1, wherein an inner surface of a distal end of the secondary fluid chamber defines a seating surface for abutting engagement with the distal end surface of the secondary stopper when the secondary stopper is completely advanced within the barrel, thereby isolating the secondary fluid chamber from the outlet lumen and the outlet of the valve.

6. The syringe of claim 1, wherein the reciprocating needle has a Luer connector profile.

7. The syringe of claim 6, wherein a tip of the needle abuts a valve seat formed in the proximal end surface of the primary stopper when the needle is oriented in the closed engagement position and wherein the needle tip is axially spaced away from the valve seat when the needle is oriented in the open engagement position.

8. The syringe of claim 1, wherein a tip of the needle abuts a valve seat formed in the proximal end surface of the primary stopper when the needle is oriented in the closed engagement position and wherein the needle tip is axially spaced away from the valve seat when the needle is oriented in the open engagement position.

9. A syringe comprising:

a substantially cylindrically shaped barrel which defines an inner side wall, the barrel having an open proximal end and a distal end, the distal end of the barrel including a connector defining an outlet lumen therethrough, the outlet lumen in fluid communication with an interior of the barrel, the interior defined by the open proximal end, the distal end, and the inner side wall;

nested primary and secondary plungers disposed within the interior of the barrel, respectively having primary and secondary plunger rods capable of selective translation within the interior of the barrel along a common axis, the primary plunger rod being a tubular and defining a cam slot with open and closed engagement surface portions;

a primary stopper coupled to a distal end of the primary plunger, the primary stopper having a proximal end surface facing the proximal end of the barrel and a distal end surface facing the distal end of the barrel, the primary stopper defining a through aperture between its proximal and distal end surfaces in fluid communication with the outlet lumen;

a secondary stopper coupled to a distal end of the secondary plunger, the secondary stopper having a distal end surface facing the distal end of the barrel;

a resealable valve formed by the primary stopper and a spring-loaded reciprocating needle aligned along the common axis, the resealable valve oriented within the tubular primary plunger rod of the primary plunger, along the common axis toward the distal end of the barrel away from the distal end surface of the secondary stopper, the reciprocating needle opening the valve in an open engagement position in which the distal end surface of the secondary stopper is in fluid communication with the through aperture of the primary stopper through an aperture of the primary plunger rod, the reciprocating needle closing the valve in a closed engagement position, wherein the reciprocating needle includes with a radially projecting cross-pin retained with the cam slot, a tip of the needle abutting a valve seat formed in the proximal end surface of the primary stopper when the cross-pin is oriented in a closed engagement surface portion of the cam slot and the needle tip axially spaced away from the valve seat when the cross-pin is oriented in an open engagement surface portion of the cam slot;

a primary fluid chamber within the barrel interior of the barrel defined between the distal end surface of the primary stopper and the distal end of the barrel, a volume of the primary fluid chamber being selectively variable by translation of the primary plunger rod; and a secondary fluid chamber within the barrel interior of the barrel defined between the distal end surface of the secondary stopper and a valve inlet defined by the aperture of the primary plunger rod and in fluid communication with the aperture of the primary plunger rod, a volume of the secondary fluid chamber being selectively variable by translation of the secondary plunger rod;

wherein, when the valve is closed, the secondary fluid chamber is isolated from the outlet lumen so that translation of the primary plunger rod only aspirates fluid into or dispenses fluid out of the primary fluid chamber via the outlet lumen; and wherein, when the valve is open, the secondary fluid chamber is in fluid communication with the outlet lumen so that translation of the secondary plunger rod aspirates fluid into or dispenses fluid out of the secondary fluid chamber via the outlet lumen.

10. The syringe of claim 9, further comprising a spring biasing the needle away from the valve seat.

11. The syringe of claim 9, wherein the secondary plunger is tubular and the primary plunger is therein in the secondary plunger, and the secondary stopper having an annular cross-section with an outer diameter of the secondary stopper abutting the inner side wall of the barrel and an inner diameter of the secondary stopper abutting an outer side wall of the tubular secondary plunger.

12. The syringe of claim 9, wherein an inner surface of the distal end of the barrel defines a seating surface for abutting engagement with the distal end surface of the primary stopper when the primary stopper is completely advanced within the barrel, thereby isolating the primary fluid chamber from the outlet lumen and an outlet of the valve formed by the through aperture of the primary stopper.

13. The syringe of claim 12, wherein an inner surface of a distal end of the secondary fluid chamber defines a seating surface for abutting engagement with the distal end surface of the secondary stopper when the secondary stopper is completely advanced within the barrel, thereby isolating the secondary fluid chamber from the outlet lumen and an outlet of the valve formed by the through aperture of the primary stopper.

14. The syringe of claim 9, wherein an inner surface of a distal end of the secondary fluid chamber defines a seating surface for abutting engagement with the distal end surface of the secondary stopper when the secondary stopper is completely advanced within the barrel, thereby isolating the secondary fluid chamber from the outlet lumen and the outlet of the valve formed by the through aperture of the primary stopper.

15. The syringe of claim 9, wherein the needle has a Luer connector profile.

16. The syringe of claim 9, wherein a proximal end of the needle extends axially outside of the tubular primary plunger rod, for selectively orienting the cross-pin in the cam slot by manipulating the proximal end of the needle.

17. The syringe of claim 16, wherein the cam slot is axially oriented parallel to the common axis, with the open and closed engagement surface portions are axially spaced relative to each other, perpendicular to and cojoined with the cam slot, and the cam slot and both engagement surface portions pass through an entire thickness of the tubular primary plunger rod.

18. The syringe of claim 9, wherein the cam slot is axially oriented parallel to the common axis, with the open and closed engagement surface portions are axially spaced relative to each other, perpendicular to and cojoined with the cam slot, and the cam slot and both engagement surface portions pass through an entire thickness of the tubular primary plunger rod.

* * * * *